United States Patent [19]
Purser et al.

[11] Patent Number: 5,922,702
[45] Date of Patent: Jul. 13, 1999

[54] ECDYSONES USED TO IMPROVE PRODUCTIVITY OF RUMINANTS

[75] Inventors: Douglas Barrie Purser, Wembly Downs; Suzanne Kay Baker, West Perth, both of Australia

[73] Assignee: Commonwealth Scientific and Industrial Research Organisation, Campbell, Australia

[21] Appl. No.: 08/920,868

[22] Filed: Aug. 29, 1997

Related U.S. Application Data

[63] Continuation of application No. 08/507,225, filed as application No. PCT/AU94/00075, Feb. 18, 1994, abandoned.

[30] Foreign Application Priority Data

Feb. 19, 1993 [AU] Australia .................. PL7397

[51] Int. Cl.⁶ .................................................. A61K 31/575
[52] U.S. Cl. ............................................ 514/181; 514/171
[58] Field of Search ............................................ 514/181

[56] References Cited

U.S. PATENT DOCUMENTS 4,346,081  8/1982  Gago et al. .............................. 424/130
4,891,219  1/1990  Karr, Jr. et al. ........................ 424/85.8

OTHER PUBLICATIONS

Shanta. Agricola 71:98920, abstract, 1969.

Laurena, In Vitro Cell Dev. Biol., 27A:487–496, Jun. 1991.

Messer et al. Microb Ecol, 18:275–284, 1989.

Shah et al, Steroids 53(3–5):559–565, Mar. 5, 1989.

Patent Abstracts of Japan, C–121, p. 91, JP 57–81499 (Otsuka Seiyaku K.K.) May 21, 1982.

Patent Abstracts of Japan, C503, p. 3, JP 63–2928 (Japan Bio Kenkyusho K.K.) Jan. 7, 1988.

Patent Abstracts of Japan, C939, p. 50, JP 5–21696 (Sanwa Shiyouyaku K.K.) Jan. 24, 1992.

Patent Abstracts of Japan, C974, p. 129, JP 4–124135 (Beritasu K.K.) Apr. 24, 1992.

*Primary Examiner*—Rebecca Cook
*Attorney, Agent, or Firm*—Jacobson, Price, Holman & Stern, PLLC

[57] ABSTRACT

A method of improving the productivity of a ruminant animal comprising administering to said animals an effective amount of an ecdysone compound.

17 Claims, 5 Drawing Sheets

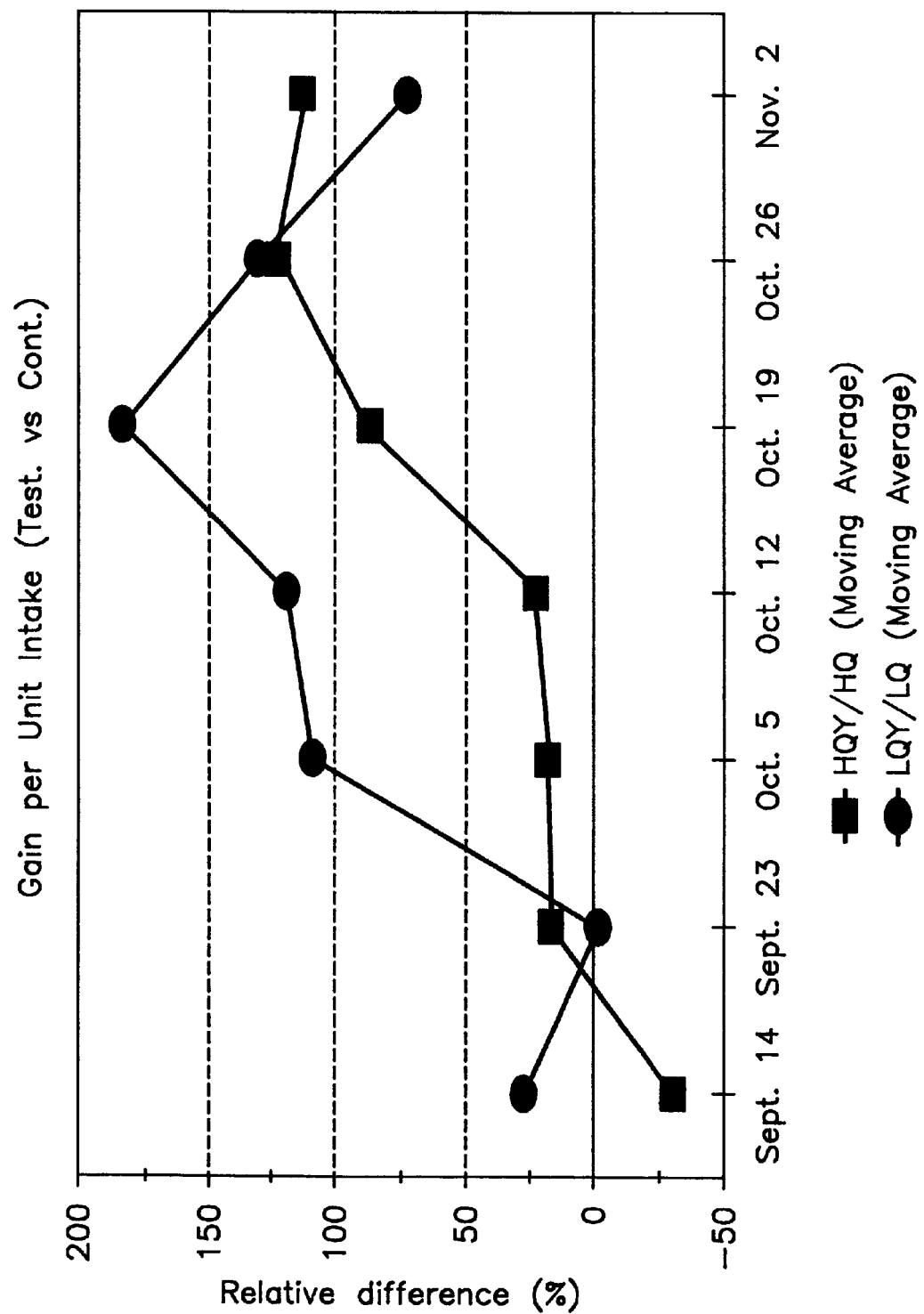

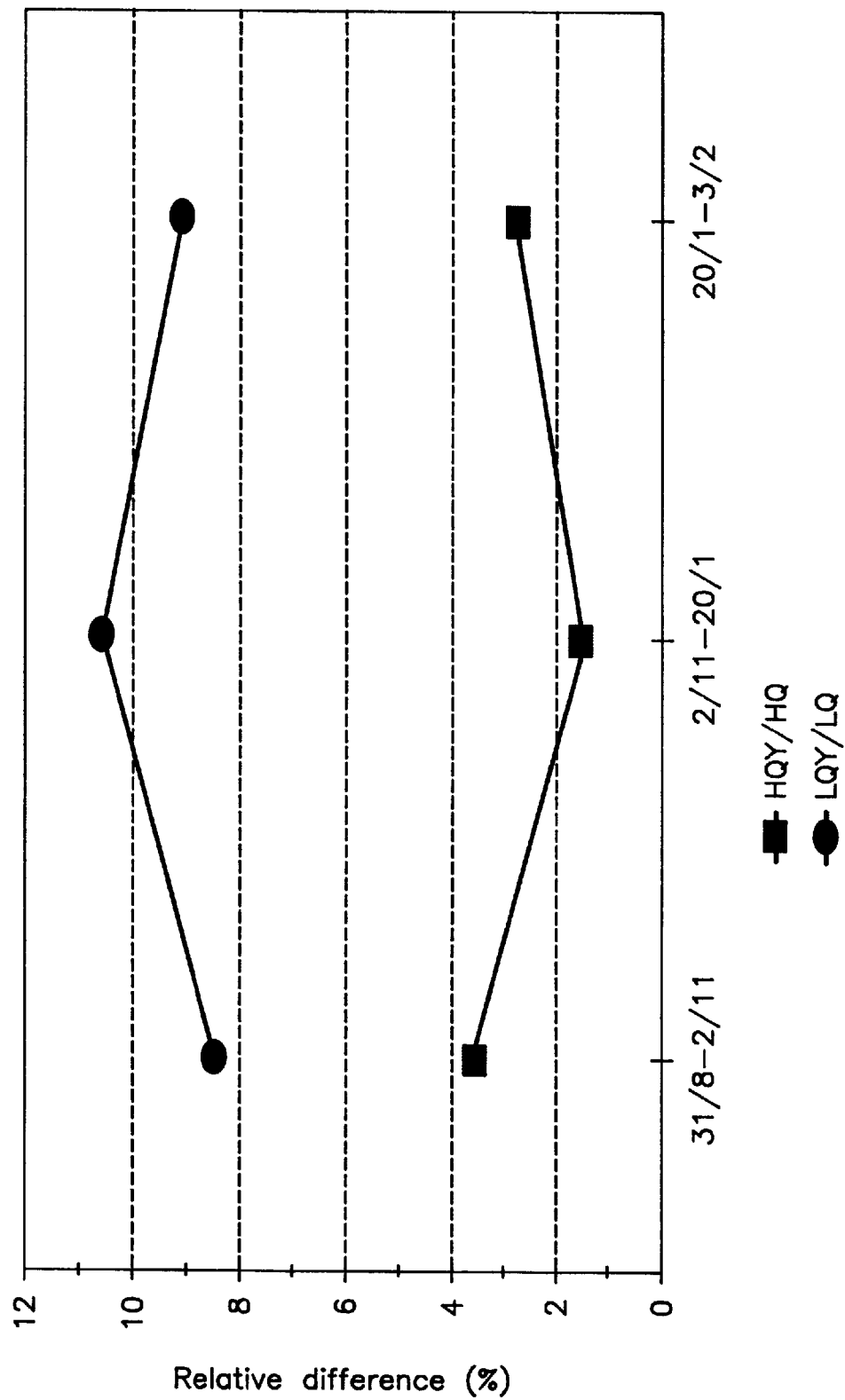

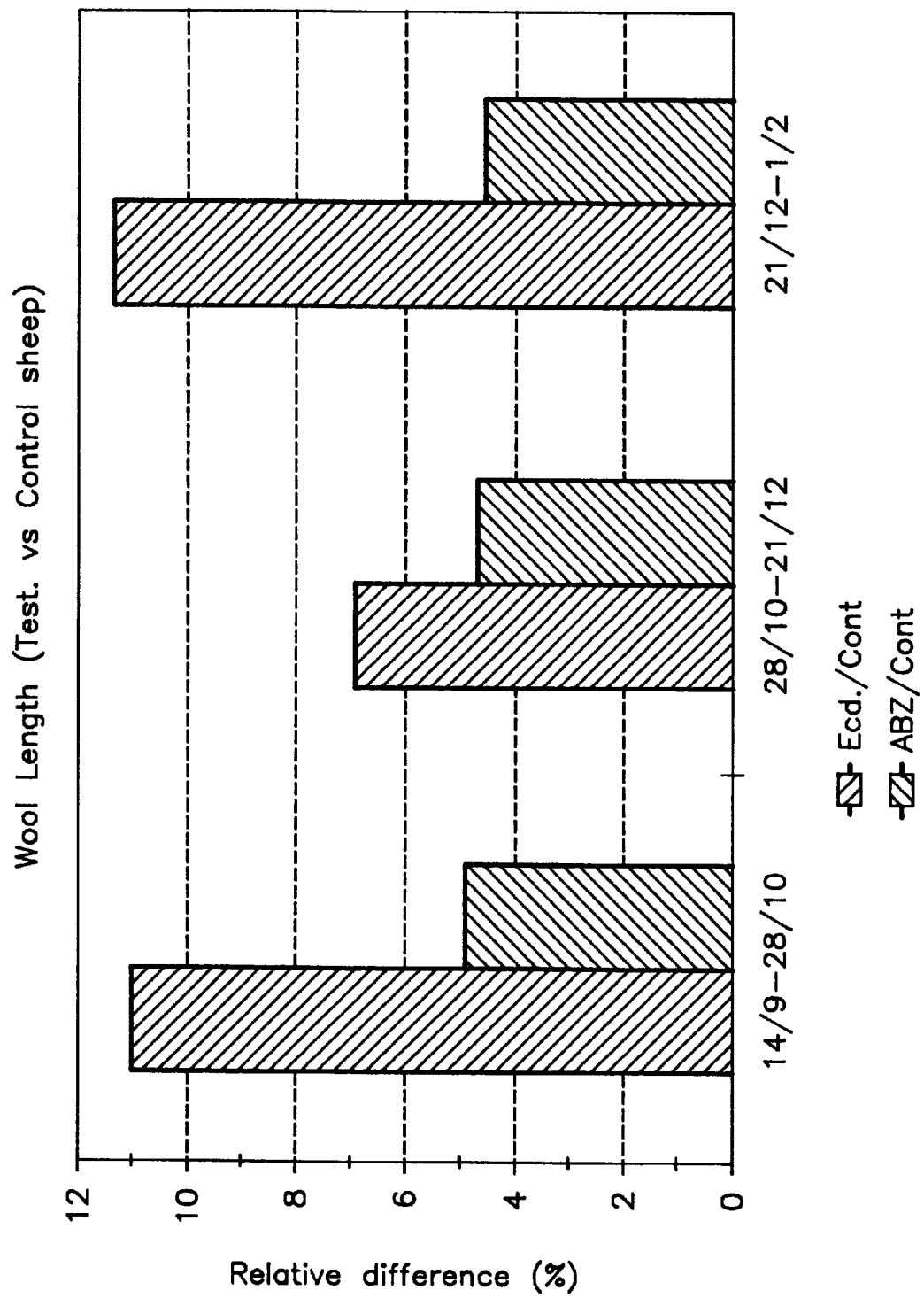

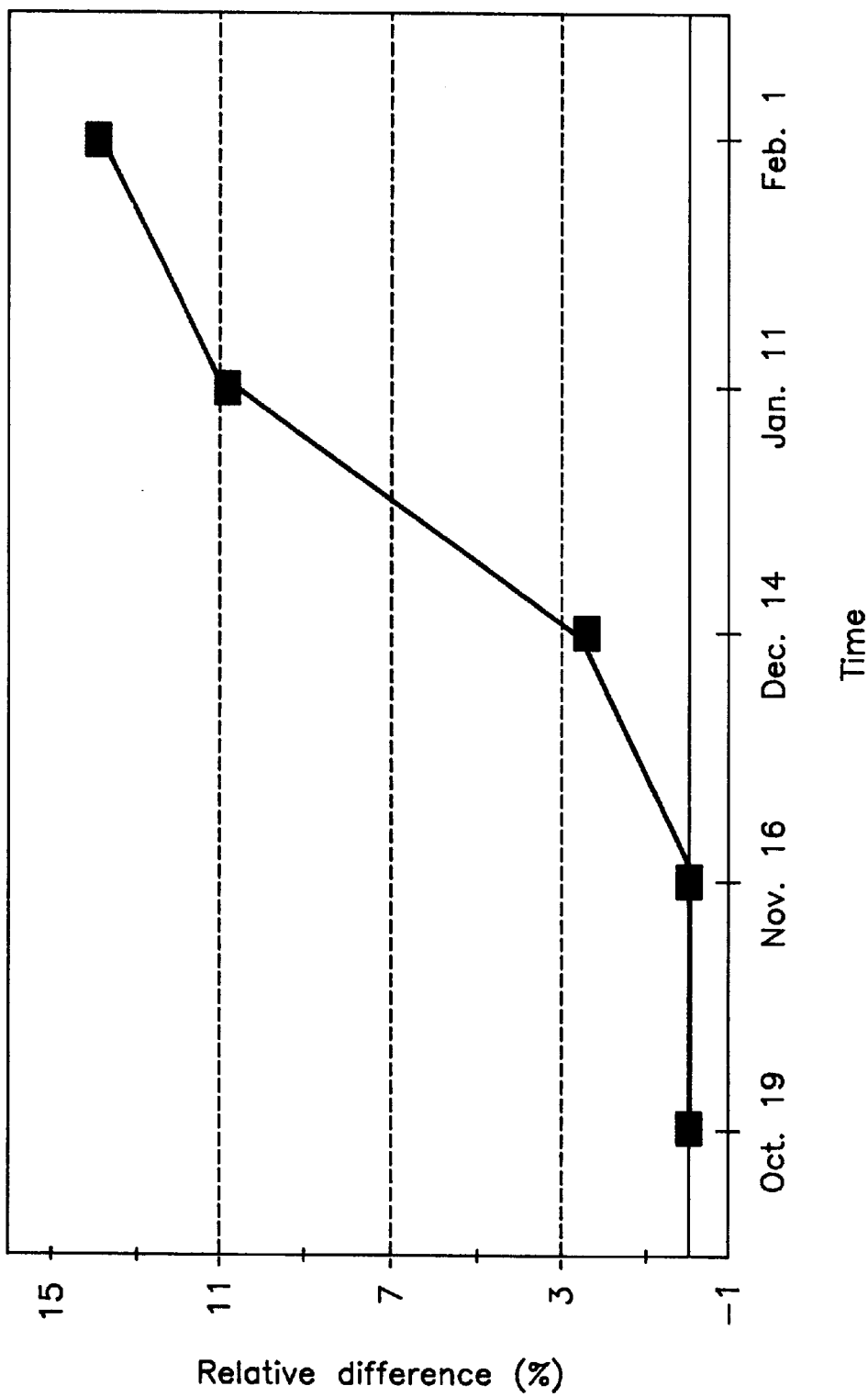

ECDYSONES USED TO IMPROVE PRODUCTIVITY OF RUMINANTS

This is a continuation of application Ser. No. 08/507,225, filed Feb. 22, 1996 which was abandoned upon the filing hereof; which is a 371 of PCT/AU 94/00075 filed Feb 18, 1994.

THIS INVENTION relates to a method of improving the productivity of ruminant or ruminant-like animals. In this respect, for simplicity, throughout the following description reference will only be made to "ruminant". Thus, the term "ruminant animals" must be understood to include "ruminant-like animals". Furthermore, where reference is made to a "rumen" it will be understood that the term is being used so as to include the "paunch" of an animal classified as a "ruminant-like" animal.

It is well known that micro-organisms in the rumen play a major role in determining the availability of nutrients. Under certain nutritional conditions, such as high-energy/low-protein diets, poorly digestible forage based rations, and the conditions experienced by grazing and pen-fed animals, the activities of protozoa in the rumen can seriously reduce the productivity of the animal. This may result in a need to supply dietary supplements, which can be relatively expensive and labor intensive to distribute.

Experimentally, it has been shown that under such conditions, defaunation (in other words, elimination of protozoa) results in an improved ratio of protein to energy of the nutrients available for absorption from the gastro intestinal tract, the advantages of which can be improved meat, wool and milk production.

Various techniques for eliminating rumen protozoa have been investigated including chemical treatments, the isolation of animals at birth to preclude the establishment of a protozoa population and the manipulation of fractional outflow rate of fluid from the rumen. None of these techniques have been used on a wide scale. Detergents, such as alkanates or terics and other chemicals which have been advocated for rumen defaunation, unfortunately tend to disrupt feed intake. These and others techniques have not found favor because of their impracticality or inefficiency.

The present invention is based on the use of certain compounds which have been found to be effective in altering the activity of rumen protozoa, these compounds being effective in smaller doses than compounds previously investigated.

The present invention provides a method of improving the productivity of ruminant animals which comprises administering to said animals an amount of a compound selected from the class of compounds known as ecdysones. In this respect, the ecdysones are molting hormones of insects and crustaceans, and they are also found in some plants.

The invention further provides a method of improving the productivity of ruminant animals, the method comprising administering to said animals an amount of an ecdysone compound with the formula 2,3,14,22,25-pentahydroycholest-7-en-6-one, or an analogue thereof.

Other compounds which display similar properties, which may be considered as analogues for the purposes of this invention, are 2,3,14,20,22,25-hydroxycholest-7-en-6-one, and the 20-hydroxyecdysones, ecdysterones, crustecdysones, isoinokosterones and other similar compounds. Further ecdysones which may be considered as analogues for the purposes of this invention are described by Nakanishi in the literature, (Nakanishi,K (1971) "The Ecdysones", Pure and Applied Chemistry 25, 167–195)

The method of the invention makes it possible for animals to have an improved productivity. In this respect, and as will be illustrated by the examples below, animals to which the method is applied show improved characteristics, such as improved body weight gain, improved wool growth (for sheep), possibly improved milk production, and also improved meat quality by virtue of a lower fat content. These aspects of improved productivity are improvements over the normal characteristics of those same animals when not subjected to the method of the invention.

However, while the improved productivity is able to be evidenced by the examples, there is some doubt as to the actual mechanism occurring in animals subjected to the method which gives rise to the improved productivity. It is believed that the method of the invention makes it possible for animals to increase the ratio of protein to energy available for absorption in the gastro-intestinal tract by controlling rumen protozoa. It is envisaged that the control of the rumen protozoa occurs via a reduction in the number of rumen protozoa, a reduction in the reproduction of rumen protozoa and/or a reduction in the activity of rumen protozoa.

As protozoa are naturally present in the rumen of the vast majority of ruminant animals it will be appreciated that animals exposed to the invention are thus considered healthy animals and actually signify the normal population of any given animal species.

Thus, otherwise healthy animals are able to be subjected to the method of the invention so that they have an improved productivity from a more efficient utilisation of ingested nutrients and/or an enhanced intake of feed. For example, animals subjected to the method of the invention may be able to meet their normal dietary requirements from a reduced amount of food or from a food supply of reduced quality.

Suitable doses of an ecdysone may be administered to animals in order to be effective in improving the productivity of the animals. Thus, the invention also provides a method of improving the productivity of ruminant animals, the method comprising administering to the animals an amount of an ecdysone compound, the amount being between 0.005 micrograms/kilogram bodyweight/day and 0.05 micrograms/kilogram bodyweight/day. Preferably the dose of ecdysone is about 0.02 mirograms/kilogram bodyweight/day.

Preferably the ecdysone compound is administered orally or intravenously. However, the compound may be administered to an animal by any one of a number of means that would be apparent to one skilled in the art, and in particular may be administered by the use of a controlled release device to sustain a predetermined dose level over a long period of time. For example, the compound may be administered by using a device and controlled release composition in accordance with that described in either or both of Australian patents 520409 and 555998.

The compound for use with the method of the invention may be provided as a veterinary preparation comprising an amount of an ecdysone compound (the compound preferably being 2,3,14,22,25-pentahydroycholest-7-en-6-one, or an analogue thereof) and a physiologically acceptable carrier. In this respect, a suitable carrier will be selected according to the particular type of animal with which the method is being used. Again, compositions as described in Pat. Nos. 520409 and 555998 may be utilised.

The veterinary preparation may also of course comprise another veterinary pharmaceutical such as, but not limited, to an antihelminth compound such as ABZ.

The present invention will now be described in relation to various examples. The examples illustrate various aspects of the invention, but are in no way intended to limited the scope thereof.

For each of the examples below, an ecdysone compound was obtained commercially. An ecdysone compound known as alpha-ecdysone was obtained from Sigma Chemical Company. Alpha-ecdysone is 2beta, 3beta, 14alpha, 22, 25-pentahydroxy-7-cholesten-6-one.

BRIEF DESCRIPTION OF THE DRAWINGS

FIGS. 1–3 illustrate the effects of α-ecdysone on weight gain and wool growth in ruminant animals.

EXAMPLE 1

Figure 2B:
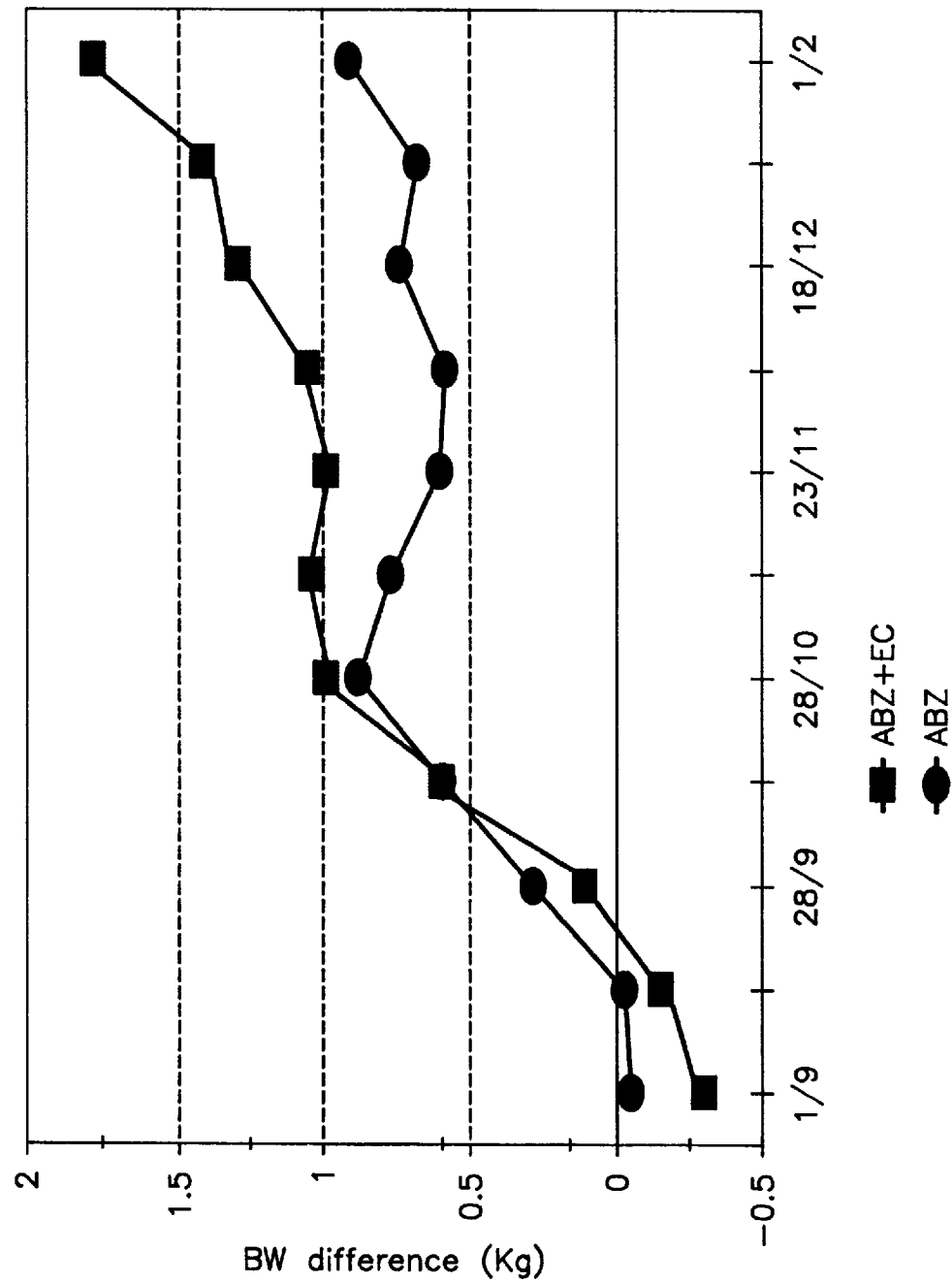

Response of sheep to defaunation using an ecdysone compound in animal house trials.

FIG. 1A illustrates the differences in body weight gain per unit of dry matter intake (DMI), between sheep on high and low quality hay in the presence and absence of alpha-ecdysone. Sheep given alpha-ecdysone on the high quality hay diet showed an increased body weight gain per unit of DMI relative to the control group which was sustained throughout the experiment and reached 125% of the body weight gain per unit intake displayed by the sheep without alpha-ecdysone.

Sheep given alpha-ecdysone on the low quality hay diet (LQY) showed an increased body weight gain per unit intake which was evident throughout the experiment and reached 180% of the body weight gain per unit intake of the sheep without alpha-ecdysone.

FIG. 1B illustrates the increased wool growth of sheep given beta-ecdysone. Sheep given alpha-ecdysone on the high quality hay diet displayed a sustained increase in wool growth over the experimental period of approximately 1.5% to 3.5% greater than wool growth of control sheep.

Sheep given alpha-ecdysone on the low quality hay diet displayed a more pronounced increase in wool growth, the increase being sustained over the experimental period and being of the order of approximately 8.5% to 10.5% greater, than the wool growth of the control sheep.

EXAMPLE 2

Effect of an ecdysone compound, administered by a controlled release device (CRD), upon grazing sheep.

This example involves the comparison of wool growth and body weight change in control sheep and sheep given alpha-ecdysone whilst grazing. Ninety sheep were selected, 30 sheep each forming a test and two control groups. Wool growth was measured in 15 sheep in each group.

The sheep were given alpha-ecdysone in a controlled release device which contained a commonly used antihelminth agent-ABZ (albendazole). The first control group were not given any alpha-ecdysone or ABZ untreated and the second control group were given ABZ alone.

FIG. 2A illustrates the effect of alpha-ecdysone on the wool growth of grazing sheep. The sheep given ABZ alone showed a sustained higher wool growth of approximately 5% when compared with the first control group. Sheep given ecdysone as well as ABZ showed higher wool growth of between approximately 7% to 11.5% when compared to the first control group and a higher wool growth of between approximately 3% to 7.5% when compared to the second control group given ABZ.

FIG. 2B illustrates the relative body weight gain (BW) of sheep given ABZ and alpha-ecdysone, sheep in the second control group given ABZ alone and sheep in the first control group. ABZ alone resulted in an increase in body weight of 0.9 kg per sheep, relative to sheep in the first control group. Alpha-ecdysone and ABZ resulted in a more substantial increase of approximately 1.75 kg per sheep, relative to the sheep in the first control group. Thus addition of alpha-ecdysone resulted in a further increase of approximately 0.85 kg per sheep.

EXAMPLE 3

Effect of an ecdysone compound administered by controlled release device (CRD), upon grazing cattle.

In this example, alpha-ecdysone was delivered to cattle using CRD's to measure the response in body weight. The dose of alpha-ecdysone per unit of body weight was the same as for sheep. Twelve cattle were separated into a control group and a test group of six cattle each.

FIG. 3 illustrates the body weight gain of the test group relative to that of the control group. Alpha-ecdysone enhanced the body weight gain of the cattle in the test group by approximately 13.5% relative to the cattle of the control group.

Other aspects of the present invention, and modifications and variations thereto, will be apparent to those skilled in the art on reading this specification, and all such other aspects and modifications and variations are to be considered as included within the scope of this invention.

We claim:

1. A method for improving the productivity of a ruminant animal comprising administering to the digestive tract of said animal an effective amount of an ecdysone compound said compound improving the productivity by effectively reducing the number, reproduction or activity of rumen protozoa.

2. The method according to claim 1 wherein the ecdysone compound is selected from the group consisting of α-ecdysone and β-ecdysone.

3. The method according to claim 2 wherein the compound is α-ecdysone.

4. The method according to claim 2 wherein the compound β-ecdysone.

5. The method according to claim 1 wherein the effective amount of the compound administered is between 0.005 micrograms/kilogram of bodyweight/day and 0.05 micrograms/kilogram of bodyweight/day.

6. The method according to claim 1 wherein the amount of the compound administered is 0.02 micrograms/kilogram of bodyweight/day.

7. The method according to claim 1 wherein the compound is administered intra-ruminally.

8. The method according to claim 1 wherein the compound is administered orally.

9. The method according to claim 1 wherein the compound is administered using a controlled release device.

10. The method according to claim 1 wherein the compound is in a gelatin capsules.

11. The method according to claim 1 wherein an amount of another veterinary pharmaceutical is also administered to said animal.

12. The method according to claim 11 wherein the other veterinary pharmaceutical is an antihelminth.

13. A method for improving the productivity of a ruminant animal comprising administering to the digestive tract of said animal an effective amount of an ecdysone compound, said compound improving the productivity by effectively reducing the number of rumen protozoa.

14. A method for improving the productivity of a ruminant animal comprising administering to the digestive tract of said animal an effective amount of an ecdysone compound, said compound improving the productivity by effectively reducing the reproduction of rumen protozoa.

15. A method for improving the productivity of a ruminant animal comprising administering to the digestive tract of said animal an effective amount of an ecdysone compound, said compound improving the productivity by effectively reducing the activity of rumen protozoa.

16. The method according to claim 14 wherein the ecdysone compound is α-ecdysone or β-ecdysone.

17. The method according to claim 15 wherein the ecdysone compound is α-ecdysone or β-ecdysone.

* * * * *